United States Patent
Rose et al.

(10) Patent No.: US 12,133,747 B2
(45) Date of Patent: Nov. 5, 2024

(54) COMPUTER-ASSISTED TOMOGRAPHY SYSTEM

(71) Applicant: Otto-von-Guericke-Universität Magdeburg, Magdeburg (DE)

(72) Inventors: Georg Rose, Magdeburg (DE); Thomas Hoffmann, Magdeburg (DE); Mathias Leopold, Magdeburg (DE); Oliver Großer, Magdeburg (DE); Maciej Pech, Magdeburg (DE)

(73) Assignee: OTTO-VON-GUERICKE-UNIVERSITAT MAGDEBURG, Magdeburg (DE)

( * ) Notice: Subject to any disclaimer, the term of this patent is extended or adjusted under 35 U.S.C. 154(b) by 247 days.

(21) Appl. No.: 17/788,079

(22) PCT Filed: Dec. 16, 2020

(86) PCT No.: PCT/EP2020/086486
§ 371 (c)(1),
(2) Date: Jun. 22, 2022

(87) PCT Pub. No.: WO2021/130081
PCT Pub. Date: Jul. 1, 2021

(65) Prior Publication Data
US 2023/0030768 A1    Feb. 2, 2023

(30) Foreign Application Priority Data
Dec. 23, 2019  (DE) ...................... 10 2019 135 780.2

(51) Int. Cl.
*A61B 6/00* (2024.01)
*A61B 6/03* (2006.01)
(Continued)

(52) U.S. Cl.
CPC ............ *A61B 6/032* (2013.01); *A61B 6/0407* (2013.01); *A61B 6/12* (2013.01)

(58) Field of Classification Search
CPC ....... A61B 6/032; A61B 6/035; A61B 6/0407; A61B 6/12; A61B 6/4266; A61B 6/4452
See application file for complete search history.

(56) References Cited

U.S. PATENT DOCUMENTS

2011/0096894 A1 * 4/2011 Uehara ................ A61B 6/4233
378/19
2019/0038245 A1 2/2019 Bailey et al.

FOREIGN PATENT DOCUMENTS

DE   102013219676 A1   2/2015
DE   202015106190 U1 * 2/2016   ............. A61B 6/032
(Continued)

OTHER PUBLICATIONS

English Translation DE202015106190 (Year: 2016).*

*Primary Examiner* — Dani Fox
(74) *Attorney, Agent, or Firm* — WC&F IP

(57) ABSTRACT

The invention relates to a computer-assisted tomography (CT) system having the following features: a) at least one X-ray source, b) at least one patient couch for supporting a patient, c) at least one first X-ray detector, provided permanently or at least temporarily in the ray path of the X-rays radiated by the X-ray source through the patient couch, d) at least one second X-ray detector, provided permanently or at least temporarily in the ray path of the X-rays radiated by the X-ray source through the patient couch, e) at least one actuable drive mechanism, using which the first and/or second X-ray detector can be moved from a position in the ray path of the X-rays radiated by the X-ray source through the patient couch, to a position outside the ray path and vice versa, f) at least one electronic control device that is configured to actuate the drive mechanism.

9 Claims, 3 Drawing Sheets

Figure 1:
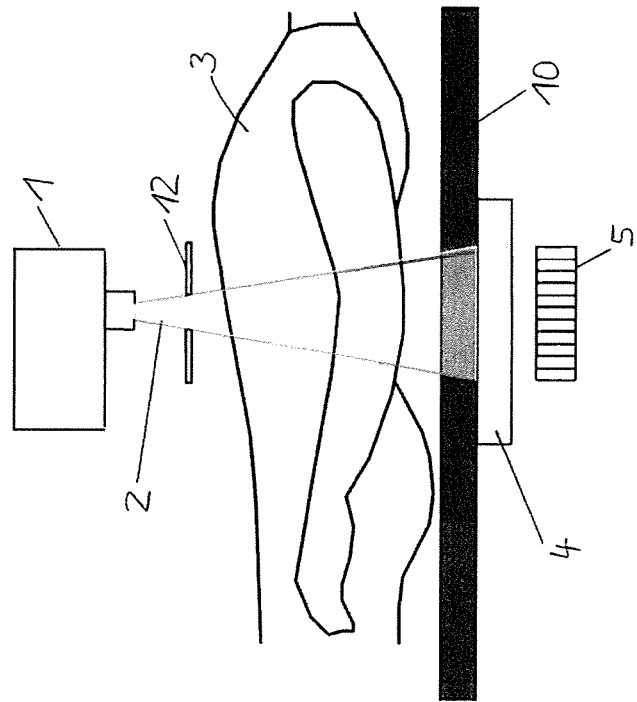

(51) Int. Cl.
*A61B 6/04* (2006.01)
*A61B 6/12* (2006.01)

(56) References Cited

FOREIGN PATENT DOCUMENTS

| | | |
|---|---|---|
| JP | 2004180755 A | 7/2004 |
| WO | 98/35613 A1 | 8/1998 |
| WO | 2008/028988 A1 | 3/2008 |

* cited by examiner

COMPUTER-ASSISTED TOMOGRAPHY SYSTEM

The invention relates to a computed tomography system, also referred to below as a CT system, for computed tomographic examinations and treatments on patients. A CT system is known, for example, from DE 10 2013 219 676 A1. CT systems may be operated with different types of X-ray detectors. One type of X-ray detector is the so-called multirow detector, which offers the advantage of imaging with a high dynamic range (contrast resolution) as well as very accurate determination of the Hounsfield values and very short integration times owing to the scintillator materials used. Flat detector systems are also used as an X-ray detector. Their advantage is a very high spatial resolution and a large imaging region.

The object of the invention is to further improve such a CT system in respect of functionality.

This object is achieved by a CT system having the following features:
 a) at least one X-ray source,
 b) at least one patient table for supporting a patient,
 c) at least one first X-ray detector, which is arranged permanently or at least temporarily in the beam path of the X-rays from the X-ray source through the patient,
 d) at least one second X-ray detector, which is arranged permanently or at least temporarily in the beam path of the X-rays from the X-ray source through the patient,
 e) at least one actuatable, for example automatically actuatable, drive mechanism by which the first and/or the second X-ray detector can be moved from a position in the beam path of the X-rays from the X-ray source through the patient to a position outside the beam path, and vice versa,
 f) at least one electronic control device, which is adapted for automatic actuation of the drive mechanism.

The CT imaging can be improved substantially by the combination of the first X-ray detector and the second X-ray detector. In particular, different working principles may be used for the first and the second X-ray detectors, for example in such a way that one X-ray detector is configured as a multirow detector and the other X-ray detector is configured as a flat detector. In this way, the advantageous properties of both working principles may be used for the CT imaging.

In addition, at least one actuatable, for example automatically actuatable, drive mechanism is provided, by which at least one of the X-ray detectors can be moved and in this way can be moved into the beam path of the X-rays or placed outside the beam path, depending on the examination and treatment situation. In this case, it is assumed that the beam path of the X-rays extends starting from the X-ray source through the patient, who is supported on the patient table. By the drive mechanism, the respective movable X-ray detector can be brought in an automated fashion to the desired position. In this way, no manual interventions are necessary. The electronic control device can correspondingly position the X-ray detector by means of the automatically actuatable drive mechanism according to the situation and requirement.

The electronic control device may, for example, comprise a computer which carries out particular control and/or regulation steps, for example by means of a computer program. The computer may be configured as a commercially available computer, for example as a PC, laptop, notebook, tablet or smartphone, or as a microprocessor, microcontroller or FPGA, or as a combination of such elements.

According to one advantageous configuration of the invention, the first and/or the second X-ray detector is physically integrated into the patient table or is arranged on the other side of the patient table as seen from the X-ray source, or can be arranged there by the drive mechanism.

The first and/or the second X-ray detectors are therefore permanent components of the CT system. By physical integration of one or both X-ray detectors in the patient table or arrangement below the patient table, space is saved so that the CT system according to the invention can be configured relatively compactly. Furthermore, the automatically actuatable drive mechanism may at least partially likewise be integrated physically into the patient table or arranged below the patient table.

According to one advantageous configuration of the invention, the first and/or the second X-ray detector may also be independent of the patient table. For example, the CT system may comprise a separate detector unit into which the first and/or the second X-ray detector is physically integrated. The first and/or the second X-ray detector may also be physically integrated into a housing of the CT system, for example on the rear side of the gantry. For example, the first and/or the second X-ray detector can be moved into or out of the opening of the CT system by means of the actuatable drive mechanism as required.

According to one advantageous configuration of the invention, the first X-ray detector is configured as a multirow CT detector. This allows particularly high-quality imaging of the individual CT image slices with a high soft tissue contrast and a high speed.

According to one advantageous configuration of the invention, the second X-ray detector is configured as a flat CT detector. This allows a very high spatial resolution and a large imaging region for the projection imaging.

The CT system may, for example, be configured in such a way that the flat CT detector can be moved by means of the automatically actuatable drive mechanism. In this case, the flat CT detector may be placed outside the beam path for the conventional CT imaging, in which the multirow CT detector is used. In this case, the conventional CT imaging may be carried out unperturbed, for example with rotation, by means of the multirow detector and the X-ray source (CT X-ray tube). If a wide imaging region is required in the form of radiography or fluoroscopy, the flat CT detector may be brought into the beam path of the X-ray source by means of the drive mechanism while being automatically controlled by the control device. For the imaging by means of the flat CT detector, the X-ray source of the CT system itself may be used. In order to allow continuous, for example fluoroscopic, imaging, the gantry rotation may be stopped or triggered imaging may take place from a fixed angle in the rotation.

According to one advantageous configuration of the invention, the second X-ray detector is configured as an angled flat CT detector or as at least two flat CT detectors arranged at an angle to one another. This allows imaging from larger lateral angles. The distortions of the patient's anatomy, which occur during the imaging, may be corrected computationally while taking the rotation parameters into account. The angle for the angled flat CT detector or for the flat CT detectors arranged at an angle to one another may, for example, lie in the range of from 130° to 170°. The angle specifications refer to a cyclometry of 360 degrees (360°).

According to one advantageous configuration of the invention, the drive mechanism is configured as an electromechanical, hydraulic or pneumatic drive mechanism or as a combination of such drive mechanisms. This allows simple and economical production of a reliable drive mechanism. The drive mechanism may, for example, comprise an electric motor for moving the respective X-ray detector, or a hydraulically or pneumatically driven actuating cylinder, or a combination of a plurality of such elements.

According to one advantageous configuration of the invention, the control device is additionally configured for control of the X-ray source and for evaluation of the signals of the first and the second X-ray detectors. In this way, all the required data are available in the control device, both in respect of the signals of the first and the second X-ray detectors and in respect of the type of irradiation by the X-ray source as well as the position of the automatically actuatable drive mechanism. In this way, additional information may be combined together, which leads to a simplification of the CT imaging and to an increase in the quality of the imaging. In this way, the overall CT system can be provided more favorably than commercially available hybrid systems.

According to one advantageous configuration of the invention, the control device is adapted to carry out the image reconstruction of the computed tomography by means of a combination of the signals of the first and the second X-ray detectors. In this way, the image information from both X-ray detectors can be incorporated into the image reconstruction, which overall allows a reduction of the X-ray dose to be applied to the patient.

According to one advantageous configuration of the invention, the CT system comprises at least one display unit for displaying images obtained from the signals of the first and/or the second X-ray detectors. The CT images and radiographs generated by the image reconstruction of the computed tomography can therefore be represented on the display unit, for example a screen.

The invention will be explained in more detail below with the aid of exemplary embodiments and the use of drawings.

Figure 4:
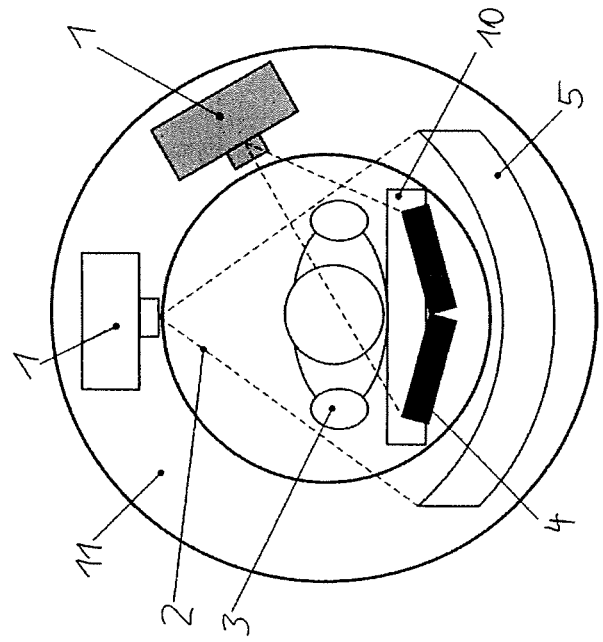
Figure 3:
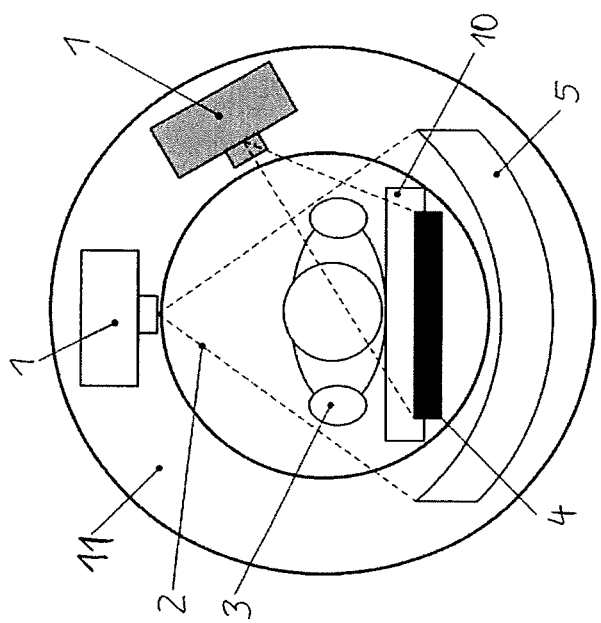
Figure 5:
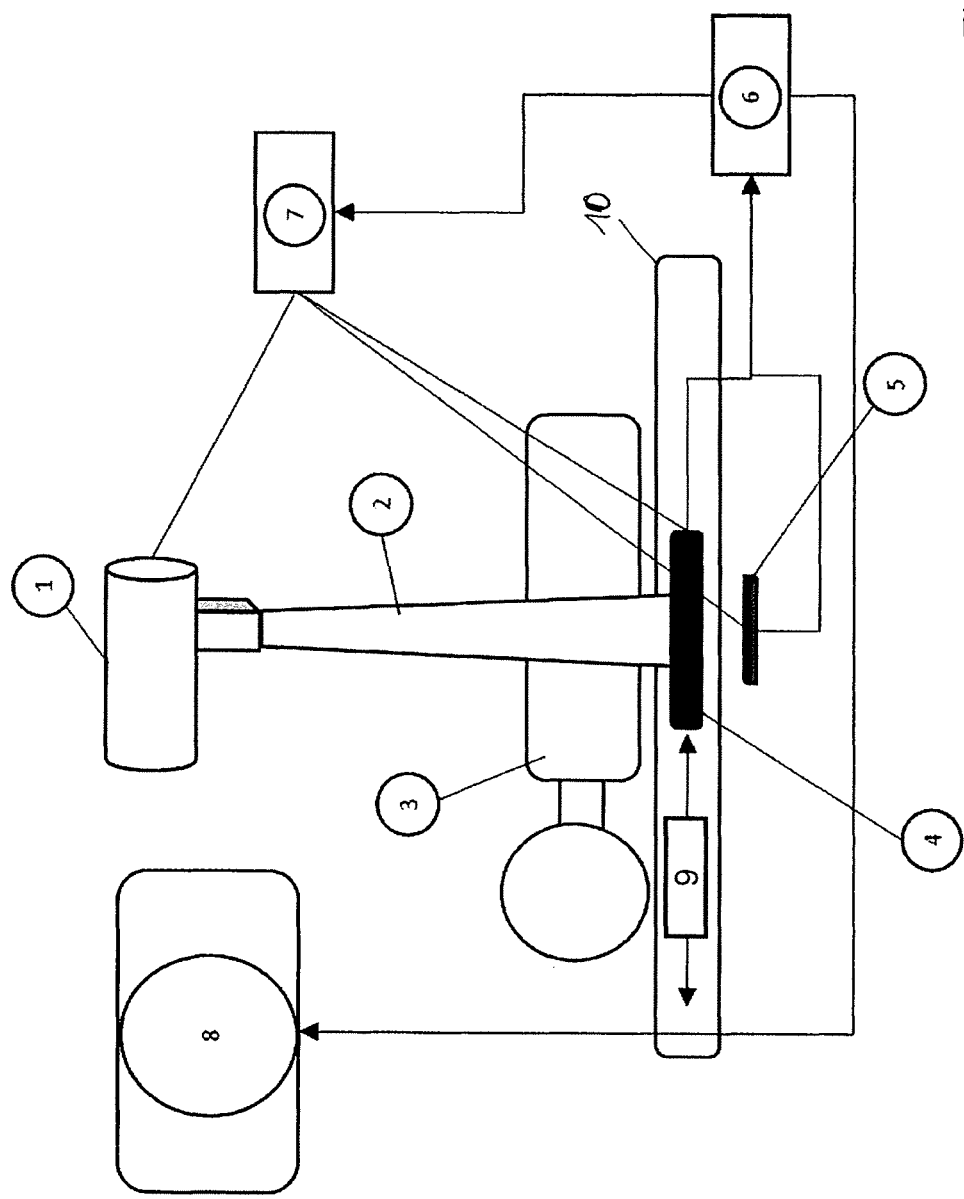

FIG. 1, 2 show a part of the CT system in a side view with a differently positioned second X-ray detector, and FIG. 3 shows a simplified frontal view in the gantry structure of the CT system, and FIG. 4 shows a further embodiment of the CT system in frontal view, and FIG. 5 shows a schematic block diagram of the overall CT system.

The CT system represented in the figures comprises an X-ray source 1, a collimator 12, a patient table 10, a first X-ray detector 5, a second X-ray detector 4, an automatically actuatable drive mechanism 9, a CT gantry 11, an electronic control device 6, 7 and a display unit 8.

Figure 2:
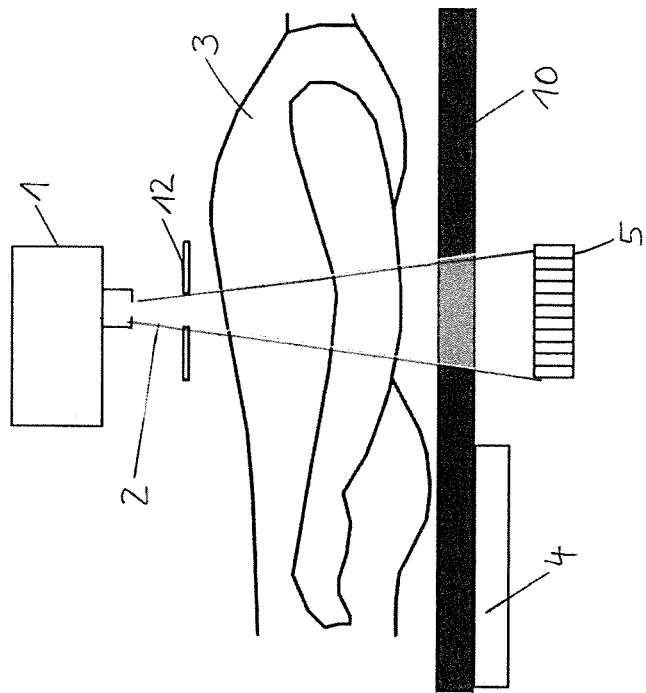

As may be seen in FIG. 1, there is a patient 3 on the patient table 10 of the CT system. The X-ray source 1 emits X-rays in a beam path 2, which are directed through the collimator 12. Adjustment of the beam path is carried out by the collimator 12. On the other side of the patient 3 from the X-ray source 1, for example below the patient table 10, there is the first X-ray detector 5, for example the conventional multirow detector. The second X-ray detector 4, for example a flat detector, is additionally present. By the drive mechanism 9 (not visible in FIG. 1), the second X-ray detector 4 can be moved from a position outside the beam path 2, as represented in FIG. 1, into a position within the beam path 2, for example a linear or tilting movement, as shown by FIG. 2. In this case, in particular, imaging may be performed by means of the signals of the second X-ray detector 4. The first X-ray detector 5 may in this case deliver at least insufficient signals for the image reconstruction. By the drive mechanism 9, the second X-ray detector 4 can be moved back from the position represented in FIG. 2 into the position represented in FIG. 1.

FIG. 3 shows the CT system according to FIG. 2 with the second X-ray detector 4 located in the beam path 2, in a frontal representation through the CT gantry 11. It is furthermore shown that the X-ray source 1, as is conventional in CT systems, can be rotated around the patient 3 at least in a certain range in order to allow CT image reconstruction from different irradiation angles. FIG. 3 in this case shows the configuration of the second X-ray detector 4 as a flat detector having a continuous plane detector surface.

FIG. 4 shows an embodiment, likewise in the same frontal representation, which is modified relative to FIG. 3 insofar as the second X-ray detector 4 is configured as an angled flat CT detector or as an arrangement of two flat CT detectors arranged at an angle to one another. In this way, a larger angle range can be covered in the signal acquisition by the second X-ray detector 4.

FIG. 5 schematically shows the overall CT system. Again shown is the X-ray source 1 with the beam path 2 of the X-rays, which extends through the patient 3 to the first X-ray detector 5 or, if the second X-ray detector 4 is moved into the beam path, also to the second X-ray detector 4. The patient 3 is again supported on the patient table 10. For example, the second X-ray detector 4 may be integrated into the patient table 10.

Also visible is the automatically actuatable drive mechanism 9 by which the second X-ray detector 4 can be moved in the manner described. The drive mechanism 9 may likewise be integrated into the patient table 10.

Furthermore represented is the signal connection between the aforementioned elements of the CT system and the electronic control device 6, 7, which may for example comprise a computer unit 6 and a controller 7. The control of the X-ray source 1, of the first and the second X-ray detectors 4, 5, and of the drive mechanism 9 may be performed by means of the controller 7. The controller 7 is coupled to the computer unit 6. In this way, the computer unit 6 can evaluate all data which are delivered by the first and the second X-ray detectors 4, 5 in combination with the control data of the controller 7, and in particular can carry out image calculation by means of a combination of the signals of the first and the second X-ray detectors 4, 5.

The CT images determined by means of the computer unit 6 may be represented on the display unit 8 coupled to the computer unit 6.

The invention claimed is:

1. A computed tomography (CT) system, comprising:
    a) at least one X-ray source,
    b) at least one patient table for supporting a patient,
    c) at least one first X-ray detector, which is arranged permanently or at least temporarily in a beam path of X-rays from the at least one X-ray source through the at least one patient table,
    d) at least one second X-ray detector, which is arranged permanently or at least temporarily in the beam path of the X-rays from the X-ray source through the at least one patient table, wherein the at least one second X-ray detector is physically integrated into the at least one patient table, and wherein the at least one second X-ray detector is configured as either an angled flat CT detector or as at least two flat CT detectors wherein the at least two flat CT detectors are arranged at an angle to one another,
    e) at least one actuatable drive mechanism by which the first and/or the second X-ray detector are moveable from a position in the beam path of the X-rays from the at least one X-ray source through the at least one patient table to a position outside the beam path of the X-rays from the at least one X-ray source, and vice versa, f) at least one electronic control device adapted for actuation of the at least one actuatable drive mechanism.

2. The CT system as claimed in claim 1, wherein the at least one first X-ray detector is arranged on a side of the at least one patient table opposite the at least one X-ray source, or is arrangeable on the side of the at least one patient table opposite the at least one X ray source by the at least one actuatable drive mechanism.

3. The CT system as claimed in claim 1 wherein the at least one first X-ray detector is configured as a multirow CT detector.

4. The CT system as claimed in claim 1 wherein the at least one second X-ray detector is configured as the angled flat CT detector.

5. The CT system as claimed in claim 1, wherein the at least one second X-ray detector is configured as the at least two flat CT detectors wherein the at least two flat CT detectors are arranged at an angle to one another.

6. The CT system as claimed in claim 1 wherein the at least one actuatable drive mechanism is configured as an electromechanical, hydraulic or pneumatic drive mechanism or as a combination thereof.

7. The CT system as claimed in claim 1 wherein the at least one electronic control device configured for control of the at least one X-ray source and for evaluation of signals from one or more of the at least one first X-ray detector and the at least one second X-ray detector.

8. The CT system as claimed in claim 7, wherein the at least one electronic control device is adapted to carry out image reconstruction of computer tomography using a combination of the signals of the first and the second X-ray detectors.

9. The CT system as claimed in claim 1, further comprising at least one display unit for displaying CT images obtained from the signals of the at least one first X-ray detector and the at least one second X-ray detector.

\* \* \* \* \*